(12) United States Patent
Seidman

(10) Patent No.: US 11,877,740 B2
(45) Date of Patent: Jan. 23, 2024

(54) INCISION-LESS FACE LIFT WITH STEERABLE NEEDLE

(71) Applicant: Michael D. Seidman, Orlando, FL (US)

(72) Inventor: Michael D. Seidman, Orlando, FL (US)

( * ) Notice: Subject to any disclaimer, the term of this patent is extended or adjusted under 35 U.S.C. 154(b) by 224 days.

(21) Appl. No.: 17/242,975

(22) Filed: Apr. 28, 2021

(65) Prior Publication Data

US 2021/0330318 A1 Oct. 28, 2021

Related U.S. Application Data

(60) Provisional application No. 63/016,461, filed on Apr. 28, 2020.

(51) Int. Cl.

| | | |
|---|---|---|
| *A61B 17/04* | (2006.01) |
| *A61B 17/062* | (2006.01) |
| *A61B 17/06* | (2006.01) |
| *A61B 17/34* | (2006.01) |
| *A61B 17/00* | (2006.01) |

(52) U.S. Cl.
CPC ........ *A61B 17/0469* (2013.01); *A61B 17/062* (2013.01); *A61B 17/3468* (2013.01); *A61B 2017/00792* (2013.01); *A61B 2017/00876* (2013.01); *A61B 2017/06176* (2013.01)

(58) Field of Classification Search
CPC .............. A61B 17/0469; A61B 17/062; A61B 2017/00792; A61B 17/3478; A61B 2017/00; A61B 2017/00743; A61B 2017/003; A61B 17/0482; A61B 17/3403; A61B 17/3469; A61B 17/3468; A61B 2017/00876; A61B 2017/0003; A61B 2017/00398; A61B 2017/06095; A61B 2017/00796

USPC ................................................. 606/139, 148
See application file for complete search history.

(56) References Cited

U.S. PATENT DOCUMENTS

| | | | |
|---|---|---|---|
| 7,494,488 B2 | 2/2009 | Weber | |
| 8,992,422 B2 * | 3/2015 | Spivey | ........... A61B 17/320016 600/102 |
| 10,595,985 B2 | 3/2020 | Lee et al. | |
| 10,646,340 B2 | 5/2020 | Manash et al. | |
| 2008/0082113 A1 * | 4/2008 | Bishop | .................... A61L 17/06 606/232 |

(Continued)

FOREIGN PATENT DOCUMENTS

WO    WO-2012037506 A2 *   3/2012   ............. A61B 34/20

*Primary Examiner* — Tan-Uyen T Ho
*Assistant Examiner* — Lindsey Bachman
(74) *Attorney, Agent, or Firm* — Fishman Stewart PLLC

(57) ABSTRACT

A method and system of enhancing facial or other body sites that are sagging, including incisionlessly inserting a lumen into a head or other areas of the body of a patient, the lumen having a first end configured to penetrate skin and a superficial musculoaponeurotic system (SMAS) of the patient, and having a first end with a suture attached thereto, a main control unit configured to translate, rotate, and flex the lumen, such that the lumen is steerable around an ear of the patient, and such that the suture remains under the skin of the face and passes through the SMAS, directing the lumen to exit the skin, detaching the lumen from the suture, and pulling taut the suture to elevate the SMAS.

19 Claims, 5 Drawing Sheets

(56) References Cited

U.S. PATENT DOCUMENTS

| | | | | |
|---|---|---|---|---|
| 2008/0108957 A1* | 5/2008 | Cumbo | ............ | A61B 17/06066 |
| | | | | 606/228 |
| 2009/0082791 A1* | 3/2009 | Schroeder | ............. | A61F 2/0059 |
| | | | | 606/151 |
| 2009/0216251 A1* | 8/2009 | Levine | ............... | A61B 17/0485 |
| | | | | 606/139 |
| 2020/0147301 A1* | 5/2020 | Grover | .................... | A61F 6/005 |

* cited by examiner

INCISION-LESS FACE LIFT WITH STEERABLE NEEDLE

CROSS-REFERENCE TO RELATED APPLICATION

This application claims the benefit of U.S. Provisional Patent Application Ser. No. 63/016,461 filed on Apr. 28, 2020, the disclosure of which is hereby incorporated by reference in its entirety as though fully set forth herein.

TECHNICAL FIELD

This disclosure relates generally to a cosmetic surgery and, more particularly, to an apparatus and method for an incision-less face, forehead and neck lift with a steerable needle.

BACKGROUND

A goal of a cosmetic facial surgery is to create a consistent, youthful, and smooth appearance. A popular type of cosmetic facial surgery is the face lift, which lifts and firms sagging facial tissues to restore a natural and youthful appearance. Currently, face lifts are typically performed by making an initial incision on the face. An incision is a cut made into the skin and tissues of a body to expose the underlying tissue, bone, or organ. An incision may include a sharp instrument that makes a clean cut into the skin, fat, the underlying tissue, and the muscle. It may also be a large cut into the skin and tissues, allowing a surgeon enough room to examine the area that is being worked on, and enough room to insert medical devices necessary for a surgery.

A traditional face lift may often include an incision that begins at the temples, continues both behind and just in front of the ear, and ends at the lower scalp. Additional incisions may be required to tighten further tissue from the neck region. The facial skin is separated from the underlying tissue and muscles, allowing a surgeon to reposition and tighten the facial tissues. Excess skin is removed from the patient and the remaining skin is then laid back over the tightened tissues to create a firmer looking appearance. The incisions are often closed with the use of sutures or staples (suboptimal) that may be either dissolvable or removed from the patient once healed.

Human skin includes at least 3 layers including the epidermis, dermis, and subdermis. Under the skin of the face is the Superficial Musculo-Aponeurotic System (SMAS). The SMAS is described as a region of fascia under the facial skin which is important for the suspension of tissues of the face and transmitting motion from facial muscles. During a face lift, surgeons reposition and tighten the tissues and muscles associated with the SMAS for a more robust and longer lasting effect.

Face lifts are currently an expensive surgery and may require 4-12 weeks to fully heal. Present surgical devices and the removal of excess skin may require incisions that can be large, take an extended time to heal from, and leave visible scars on the surface of the skin.

Therefore, a need exists for improved methods and apparatus for face lifts.

BRIEF DESCRIPTION

The disclosure is directed toward a method and system for performing an incision-less face lift with a steerable needle.

According to one aspect, a method of enhancing facial features includes incisionlessly inserting a lumen into a head of a patient, the lumen having a first end configured to penetrate skin and a superficial musculoaponeurotic system (SMAS) of the patient, and having a first end with a suture either attached thereto or a suture threaded through a needle with a micro-open bore, steering the lumen around an ear of the patient, such that the suture remains under the skin of the face and passes through the SMAS, directing the lumen to exit the skin, detaching the lumen from the suture, and pulling taut the suture to elevate the SMAS.

According to another aspect, a system for enhancing facial features includes a lumen insertable into a head of a patient, the lumen including a first end configured to penetrate skin and a SMAS of a patient, and a first end with a suture threaded thereto, and a main control unit configured to translate, rotate, and flex the lumen, such that the lumen is steerable around an ear of the patient, and such that the suture remains under the skin of the face and passes through the SMAS.

Various other features and advantages will be made apparent from the following detailed description and the drawings. For example, it will be apparent by the disclosure that the method and system disclosed could be used in various other cosmetic surgeries, for example, brow lifts, forehead lifts, neck lifts, and partial abdominal or breast lifts if so desired.

DETAILED DESCRIPTION

The method and system of the disclosed examples are described with respect to performing an incision-less limited face lift using a steerable needle and local anesthetics to positively enhance facial features, appearances, and reverse the aging look that occurs from a sagging face and relaxed superficial musculoaponeurotic system (SMAS). Examples are described with respect to a steerable needle, however it is contemplated that the disclosed examples are applicable to other medical devices as well, and may be used for cosmetic surgeries other than face lifts.

Figure 1:
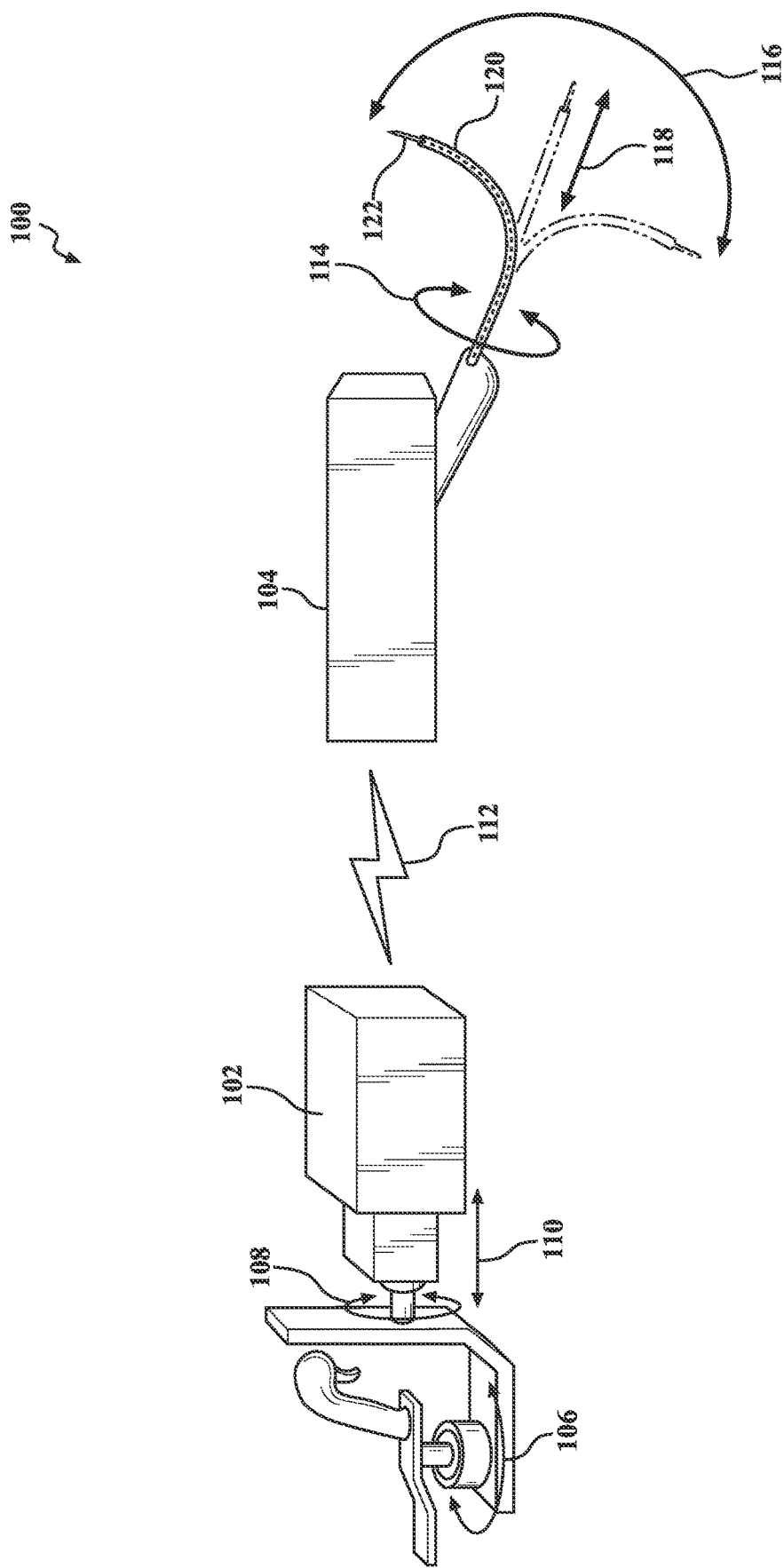
FIG. 1 is a perspective view of a steerable needle apparatus.

Referring to FIG. 1, a system for enhancing facial features 100 includes a main control unit 102 and a receiver unit 104. Main control unit 102 is configured to allow a surgeon to provide directional commands including at least commands for the rotation 106, the flexion 108, and the translation 110 of a device. Main control unit 102 is magnetically coupled 112 to receiver unit 104 such that commands provided to main control unit 102 are received and mimicked by receiver unit 104. Receiver unit 104 includes a flexible lumen 120 which is controlled by rotation 106, flexion 108, and translation 110 of main control unit 102. As such, lumen 120 is capable of rotating 114, flexing 116, and translating 118. Lumen 120 contains a first end 122 which is configured as a sharp tip, such as a needle. First end 122 shall be sharp to penetrate skin of a patient and channel through the SMAS of a patient. Lumen 120, according to the disclosure, refers generally to a scope or channel. Lumen 120 may be more generally a needle. Lumen 120 may be a sterile or flexible tube that is inserted into the body. Lumen 120 may have an open bore at a first end. Lumen 120 may be made of hollow or solid materials. Lumen 120 may be a disposable or a reusable apparatus.

Figure 2A:
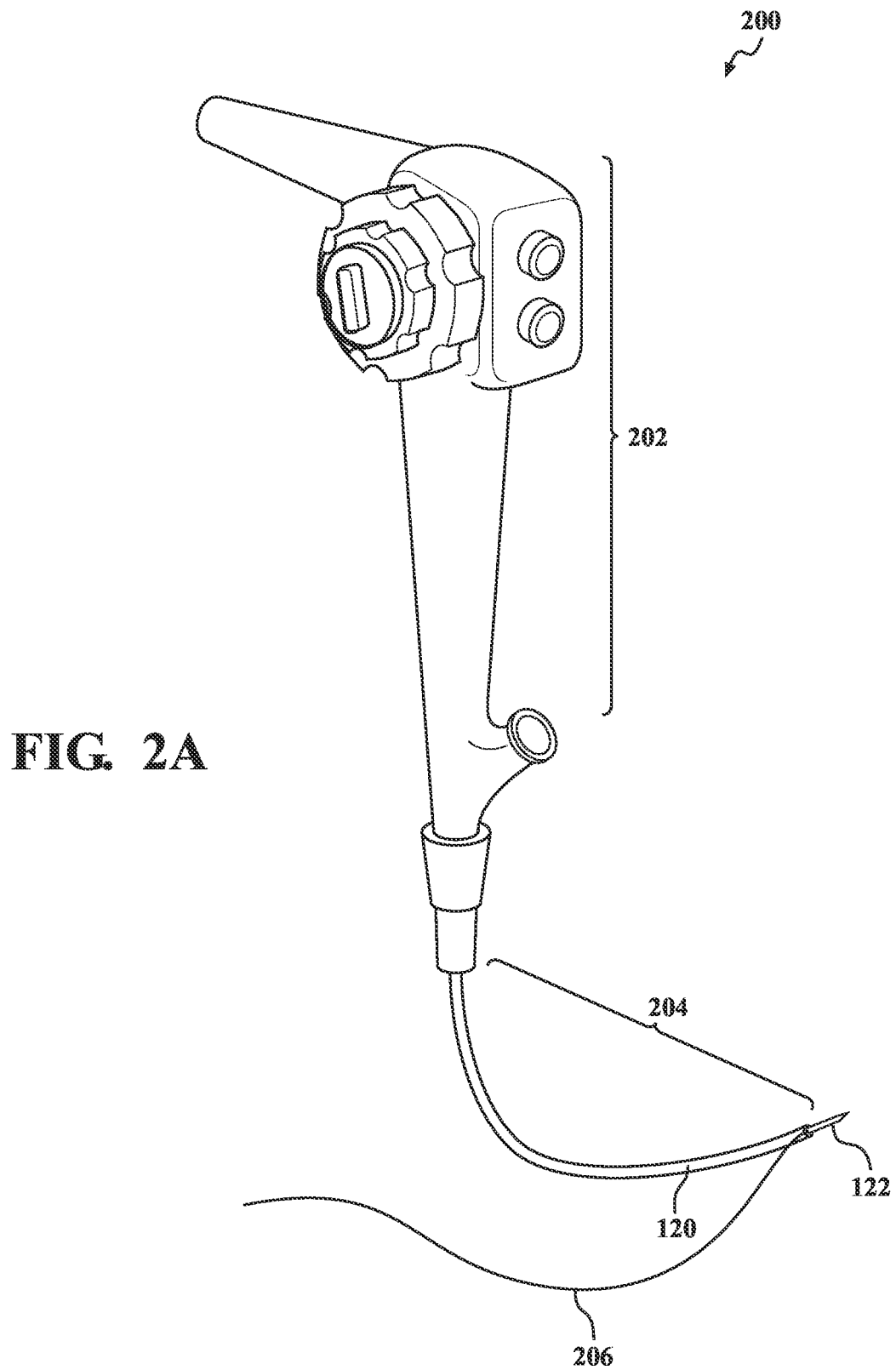
FIG. 2A is a cross-sectional view of a first example of the apparatus illustrated in FIG. 1.

FIG. 2A illustrates a first example of a medical device 200 which includes receiver unit 104. Receiver unit 104 contains a base 202 and an insertable half 204. Base 202 receives the directional commands from the main control unit 102 (not shown). Insertable half 204 is that which is inserted into the patient and includes lumen 120. Lumen 120 is capable of rotating 114, flexing 116, and translating 118 as illustrated in FIG. 1. Lumen 120 includes first end 122 that is configured to penetrate the skin and SMAS of a patient. First end 122 may be configured to be a needle between 14 gauge and 22 gauge, and preferably 18 gauge. First end 122 is a thin needle to reduce the likelihood of scaring on the patent's skin. First end 122 may be configured to be less than 4 millimeters in length, and preferably between 3 millimeters and 4 millimeters. In a first example, a suture 206 is attached to first end 122. Suture 206 may be attached through an open bore in first end 122. When first end 122 is inserted into a patient, suture 206 trails behind lumen 120 underneath the skin of the patient. Suture 206, according to the disclosure, refers generally to a medical device to hold body tissues together. Suture 206 may be a stitch or thread. Suture 206 may be barbed or smooth, and may be made of a variety of materials not limited to nylon, silk, polypropylene or polyester.

Figure 2B:
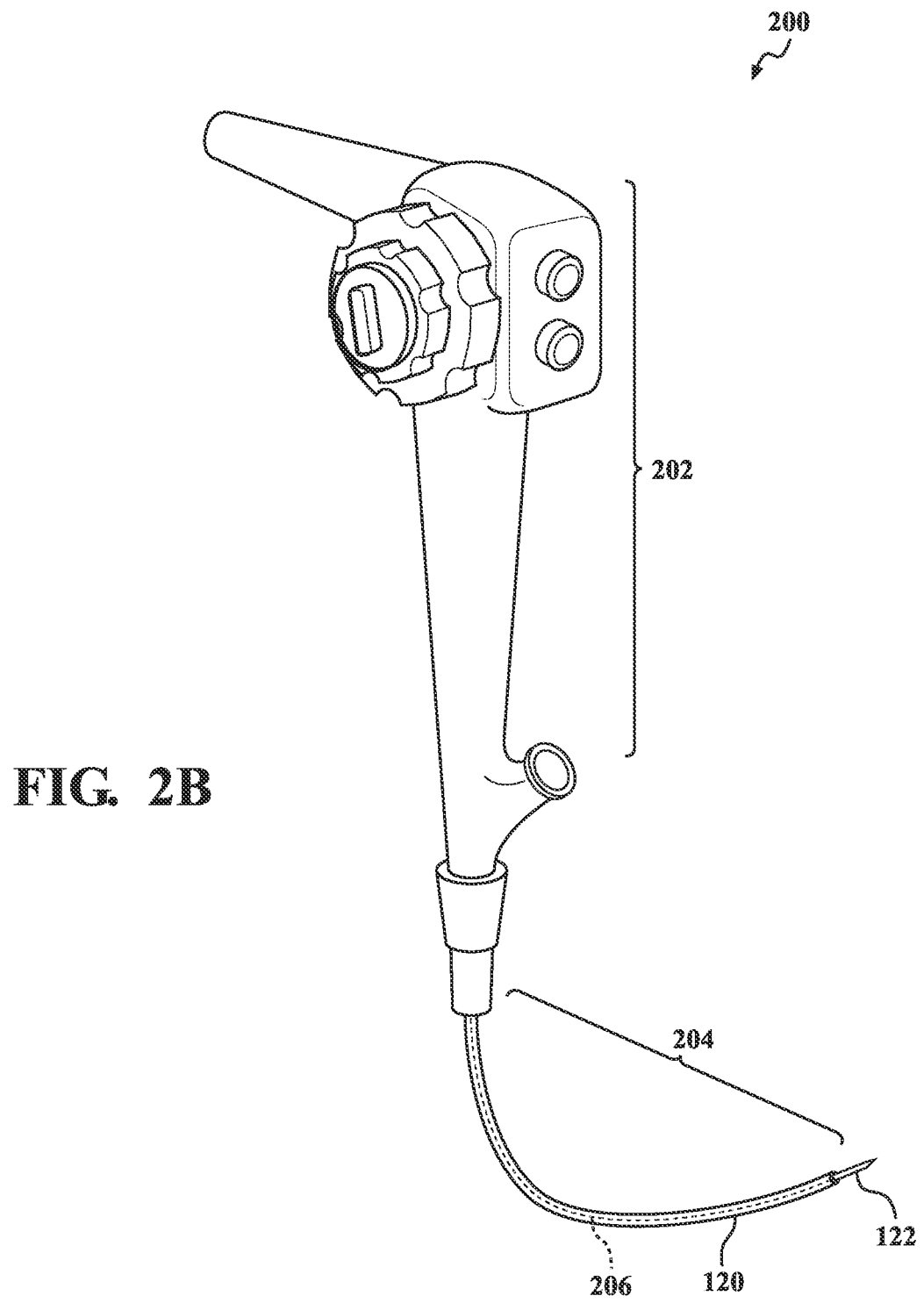
FIG. 2B is a cross-sectional view of a second example of the apparatus illustrated in FIG. 1.

FIG. 2B illustrates a second example of a medical device 200 which includes receiver unit 104. Receiver unit 104 contains a base 202 and an insertable half 204. Base 202 receives the direction commands from main control unit 102 (not shown). Insertable half 204 is that which is inserted into the patient and includes lumen 120. Lumen 120 is capable of rotating 114, flexing 116, and translating 118 as illustrated in FIG. 1. Lumen 120 includes first end 122 that is configured to penetrate the skin and SMAS of a patient. In a second example, lumen 120 includes a hollow sheath. Suture 206 is attached to first end 122 of lumen 120. Suture 206 then extends from first end 122 through a hollow sheath. When first end 122 is inserted into a patient, lumen 120 will travel underneath the skin of the patient with suture 206 inside of lumen 120.

Figure 3:
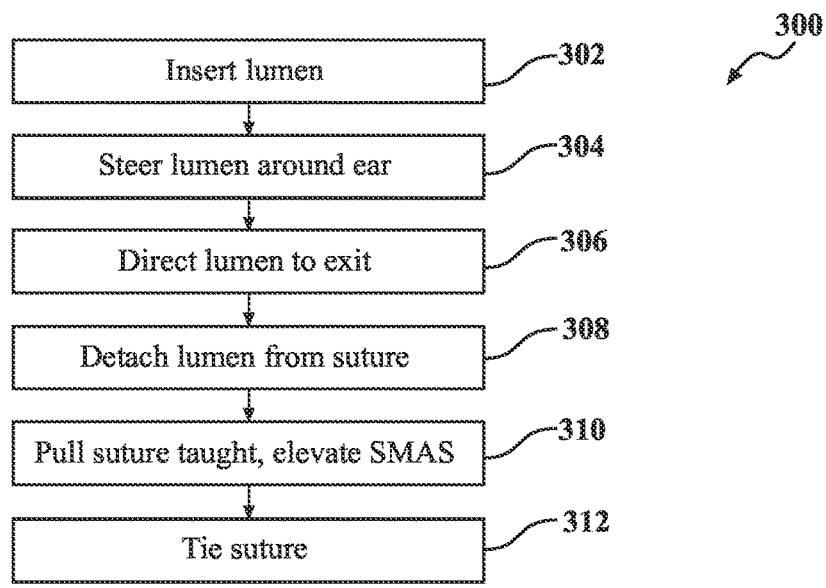
FIG. 3 shows a block diagram of the steps for performing an incision-less face lift using a steerable needle.

FIG. 3 discloses a flowchart of the method 300 for enhancing facial features according to the disclosure. At 302, method 300 includes first end 122 of a lumen 120 inserted incisionlessly into the skin of a patient. First end 122 is inserted incisionlessly by penetrating the skin with a single stab wound. First end 122 is configured as a needle. Therefore, the surgeon does not create a full incision on the head of the patient. A single stab wound from a needle will heal faster and without a scar compared to current incision-based methods. First end 122 penetrates through both the skin and the SMAS of the patient.

At 304 of method 300, lumen 120 is steered around the ear of a patient. The sharp tip of first end 122 is capable of penetrating through the underlying tissues of the face, creating a channel as it travels through the face. Lumen 120 is steered by the surgeon inputting commands into main control unit 102 for rotation 106, flexion 108, or translation 110 of lumen 120. Receiver unit 104 receives these commands and directs lumen 120 to rotate 114, flex 116, and translate 118. Once lumen 120 has channeled through the facial tissues as required for the surgery, the surgeon directs lumen 120 toward the original entrance to exit the patient at 306 of method 300. Lumen 120 is directed toward the entrance to make a substantially circle channel.

In a first example, suture 206 is attached to first end 122 as illustrated in FIG. 2A. At 302 of method 300, lumen 120 is inserted into the skin of the patient with suture 206 extending from first end 122 and trailing substantially with lumen 120. At 304 of method 300, suture 206 is steered around the ear while remaining under the surface of the skin and SMAS with lumen 120. Suture 206 shall be long enough to travel through the skin while having one end remain outside of the point of insertion.

In a second example, suture 206 is attached to first end 122 and is enclosed in a hollow sheath of lumen 120 as illustrated in FIG. 2B. At 302 of method 300, lumen 120 is inserted into the skin of the patient, with suture 206 substantially inside the hollow sheath of lumen 120. At 304 and 306 of method 300, suture 206 travels inside lumen 120 as lumen 120 is directed through the skin and SMAS of the patient.

After lumen 120 has been directed to exit the skin at 306 of method 300, the surgeon shall detach lumen 120 from suture 206 at 308 of method 300. While detaching lumen 120 from suture 206, suture 206 shall remain in the skin of the patient, encircling the ear. Suture 206 shall have a first end at or extending out of the point of insertion into the head of the patient and a second end at the point at which lumen 120 exited the head.

At 310 of method 300, the surgeon will pull suture 206 taut with both ends. Pulling suture 206 taut elevates the SMAS of the patient, providing the desired lifted appearance of a face lift. Typically, the SMAS will be elevated approximately 1 centimeter to 2 centimeters. The SMAS should be elevated no more than necessary to ensure excess skin does not need to be removed from the patient. Removing excess skin would require the skin to be cut, resulting in potential scarring of the face and a longer healing period. Once the SMAS is elevated to the appropriate height, suture 206 is tied to remain in the elevated position at step 312 of method 300.

Figure 4:
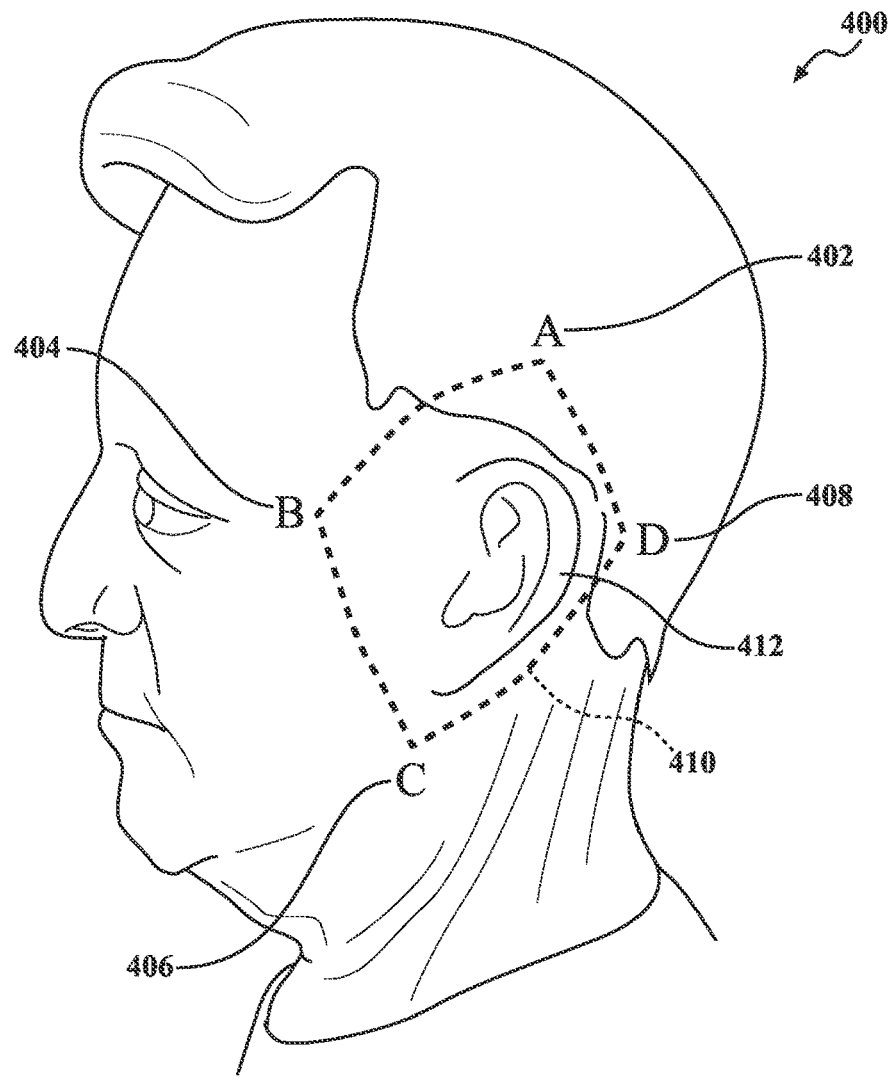
FIG. 4 shows a side view of a face with points of insertion and passage for a steerable needle during an incision-less face lift.

FIG. 4 illustrates the method of FIG. 3 using a side profile of a head 400. At 302 of method 300, lumen 120 is inserted into head 400 at or substantially near point A 402. Point A may be located posteriorly to the ear 412. Point A 402 is located posteriorly to ear 412 to be within the hairline. In the rare case a small scar should be present after the procedure, the hairline may cover a scar at point A 402. Point A 402 is also located posteriorly to ear 412 to provide the angle necessary to elevate the SMAS and achieve the desired appearance of lifted facial muscles and tissue. According to the disclosure, lumen 120 is inserted into head 400 of a patient, however it is noted that this example is directed to the facial portion of a head 400 as it deals with lifting the muscles and tissues of a face.

Once lumen 120 is inserted at point A 402, first end 122 of lumen 120 shall penetrate through the underlying tissues and SMAS of the face. At 304 of method 300, lumen 120 is steered around ear 412 of the patient using the rotation 114, flexion 116, and translation 118 controls as illustrated in FIG. 1. Lumen 120 is steered from point A 402 toward the superior portion of the SMAS at point B 404. Lumen 120 than turns and moves from point B 404 to point C 406, channeling through the underlying tissues to grasp the SMAS. Lumen 120 turns again and is directed to point D 408, creating a substantially semicircle channel around ear 412.

Finally, lumen 120 is directed to exit the skin at 306 of method 300. Lumen 120 may exit at either point A 402 or the midpoint between point A 402 and point D 408. Path 412 of lumen 120 encircles the ear, allowing suture 206 to grasp the SMAS of the patient. When the surgeon pulls suture 206 taut at 310 of method 300, the SMAS will elevate with suture 206. In another example, at 302 of method 300, a surgeon may insert lumen 120 at point D 408 and steer lumen 120 in the reverse of path 410 described above. At 306 of method 300, lumen 120 would exit at point D 408 or the midpoint between point A 402 and point D 408.

Figure 5:
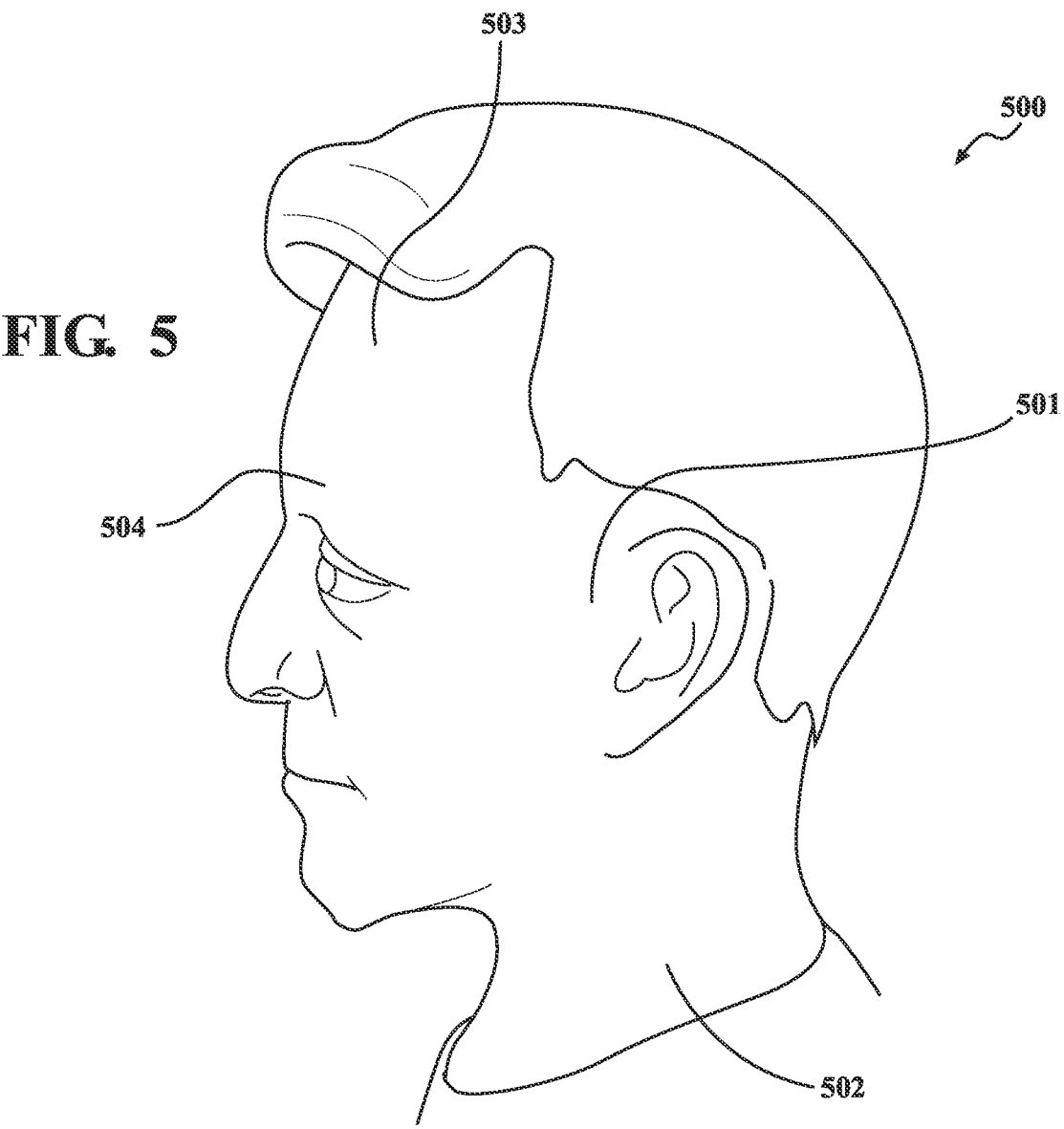
FIG. 5 shows a side view of a face with results of the disclosed surgical method.

FIG. 5 illustrates an improved outcome of undergoing the surgical method disclosed herein. On the head of the patient post-surgery 500, the patient exhibits a lifted appearance to the face 501 as a result of the disclosed method and apparatus. The disclosed method may also be used for other cosmetic surgeries to the face, head region, and other parts of the body. The patient exhibits a lifted neck 502 as a result of the disclosed method and apparatus, which may include all aspects of the neck, such as the sides of the face, under the chin, etc. . . . The patient also may benefit from a lifted forehead 503 after the disclosed method and apparatus. The patient may also receive an eyebrow lift resulting in lifted eyebrows 504. The disclosed method may also be used for other cosmetic surgeries not limited to the face and head region, such as for providing a partial abdominal lift, a breast lift, or other lifts not illustrated in FIG. 5.

According to the disclosure, a method of enhancing facial features a method of enhancing facial features thereby includes incisionlessly inserting a lumen into the face or other areas of the body that may benefit from suspension, the lumen having a first end configured to penetrate skin and a superficial musculoaponeurotic system (SMAS) of the patient, and having a first end with a suture attached thereto, steering the lumen around an ear of the patient, such that the suture remains under the skin of the face and passes through the SMAS, directing the lumen to exit the skin, detaching the lumen from the suture, and pulling taut the suture to elevate the SMAS.

Also according to the disclosure, a system for enhancing facial features includes a lumen insertable into a head of a patient, the lumen including a first end configured to penetrate skin and a SMAS of a patient, and a first end with a suture attached thereto, and a main control unit configured to translate, rotate, and flex the lumen, such that the lumen is steerable around an ear of the patient, and such that the suture remains under the skin of the face and passes through the SMAS.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of providing a face lift, it should be appreciated that the present techniques are not limited to such surgical contexts. The provision of examples and explanations in such a surgical context is to facilitate explanation by providing instances of implementations and applications. The disclosed approaches may also be utilized in other contexts, such as non-cosmetic surgeries, or cosmetic surgeries other than face lifts such as brow lifts, forehead lifts, neck lifts, partial abdominal lifts, or breasts lifts.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A method of enhancing facial features, comprising:
   incisionlessly inserting a lumen into a head of a patient, the lumen having a first end configured to penetrate skin and a superficial musculoaponeurotic system (SMAS) of the patient, and having the first end with a suture attached thereto;
   steering the lumen around an ear of the patient, such that the suture remains under the skin of the face and passes through the SMAS;
   directing the lumen to exit the skin;
   detaching the lumen from the suture; and
   pulling taut the suture to elevate the SMAS.

2. The method of claim 1, wherein the first end of the lumen is configured as a needle that penetrates skin as a single stab wound.

3. The method of claim 1, wherein incisionlessly inserting the lumen further comprises incisionlessly inserting into the head of the patient and posteriorly to the ear.

4. The method of claim 1, further comprising attaching the suture to the first end of the lumen and extending the suture therefrom.

5. The method of claim 1, wherein the lumen includes a hollow sheath.

6. The method of claim 5, wherein the suture is positioned at least partially inside the hollow sheath.

7. The method of claim 1, wherein directing the lumen to exit the skin further comprises directing the lumen such that the lumen exits the skin posteriorly to the ear.

8. The method of claim 1, wherein detaching the lumen from the suture further comprises detaching such that the suture remains under the skin and encircles the ear.

9. The method of claim 1, wherein pulling taut the suture to elevate the SMAS further comprises elevating the SMAS less than 2 cm.

10. The method of claim 9, further comprising tying the suture into a taut position.

11. A system for enhancing facial features, comprising:
    a lumen insertable into a head, neck or face of a patient, the lumen comprising:
    a first end configured to penetrate skin and a superficial musculoaponeurotic system (SMAS) of a patient, the first end with a suture attached thereto; and
    a main control unit configured to translate, rotate, and flex the lumen, such that the lumen is steerable around an ear, neck, or face of the patient, and such that the suture remains under the skin of the face and passes through the SMAS;

wherein the main control unit is magnetically coupled to a receiver unit to receive controls to translate, rotate, and flex the lumen.

12. The system of claim 11, wherein the main control unit is further configured to translate, rotate, or flex to direct the lumen to exit the skin.

13. The system of claim 11, wherein the lumen is configured to have a diameter between 14 gauge and 22 gauge.

14. The system of claim 11, wherein the first end of the lumen is configured as a needle that penetrates skin as a single stab wound.

15. The system of claim 14, wherein the needle is further configured to be less than 4 millimeters in length.

16. The system of claim 11, wherein the lumen is inserted into the head of the patient posteriorly to the ear.

17. The system of claim 11, wherein the suture is attached to the first end of the lumen and extends therefrom.

18. The system of claim 11, wherein the lumen includes a hollow sheath.

19. The system of claim 18, wherein the suture is positioned at least partially inside the hollow sheath.

* * * * *